United States Patent [19]
Frangin et al.

[11] Patent Number: 5,985,915
[45] Date of Patent: Nov. 16, 1999

[54] USE OF ANTIARRHYTHMIC COMPOUNDS IN THE PREVENTION OF POST-INFARCTION MORTALITY

[75] Inventors: Gerald Frangin, Montpellier; Alain Munoz, Fontaine-les-Dijons, both of France

[73] Assignee: Sanofi, Paris, France

[21] Appl. No.: 08/819,863

[22] Filed: Mar. 17, 1997

[30] Foreign Application Priority Data

Mar. 18, 1996 [FR] France .................................. 96 03357

[51] Int. Cl.$^6$ ...................................................... A61K 31/34
[52] U.S. Cl. ............................................................. 514/469
[58] Field of Search ............................................. 514/469

[56] References Cited

U.S. PATENT DOCUMENTS 5,223,510 6/1993 Gubin et al. ............................ 514/299

FOREIGN PATENT DOCUMENTS

WO9509625-A1 4/1995 WIPO.

OTHER PUBLICATIONS

Am. J. Cardiol., vol. 72, No. 16, 1993, pp. 70f–74f, XP000607627.
Ann. Inter. Med., vol. 122, No. 9, 1995, pp. 689–700, XP000607576.
Chew et al.—J. Cardiovasc. Pharmacoc. vol. 4 (6), 1028–36 (Abstract), 1982.
Patterson et al—Circulation (Med. Sch., Univ. of Mich.) vol. 68 (4) 857–64 (Abstract), 1983.
Seidl et al.—Ptsch. Med. Wochenschr. vol. 120 (18), 656–60, Germany (Abstract), 1995.

*Primary Examiner*—Raymond Henley, III
*Attorney, Agent, or Firm*—Jacobson, Price, Holman & Stern, PLLC

[57] ABSTRACT

The subject of the invention is a method for reducing mortality of cardiac origin in patients having a reduced left ventricular function after myocardial infarction, without rhythm disorders requiring an antiarrhythmic treatment, consisting in administering to said patients an effective amount of one or more active ingredients selected from benzofuran derivatives with antiarrhythmic activity and pharmaceutically acceptable salts thereof in combination with one or more pharmaceutically acceptable vehicles.

30 Claims, 4 Drawing Sheets

USE OF ANTIARRHYTHMIC COMPOUNDS IN THE PREVENTION OF POST-INFARCTION MORTALITY

The present invention relates, in general, to the use of antiarrhythmic compounds for the prevention of mortality following myocardial infarction.

In particular, the subject of the invention is the use of benzofuran derivatives known for their antiarrhythmic activity, in particular amiodarone, or of pharmaceutically acceptable salts of these derivatives, for the prevention of certain types of mortality following a recent myocardial infarction, especially mortality of cardiac origin, in particular cardiac mortality of arrhythmic origin.

Mortality following myocardial infarction appears at its highest, of the order of 15%, within the first 6 to 12 months following an acute accident, whereas it decreases subsequently and becomes equal to the mortality recorded in stable and chronic coronary disease.

In this context, the extent of the myocardial mass destroyed, which may be represented by the ejection fraction, as well as the ventricular arrhythmias are recognized as major risk factors.

Consequently, a medical therapy intended to prevent mortality following myocardial infarction may prove particularly indicated during the first year after the onset of this cardiac accident although a discussion is possible on the actual duration of this prophylactic therapy.

Numerous studies carried out in patients who have had a myocardial infarction confirm, however, that the left ventricular dysfunction, the ventricular arrhythmias and the extent of the coronary disease contribute independently to the risk of overall mortality and of sudden death, the left ventricular dysfunction being the essential risk factor (Multicenter Postinfarction Research Group—N. Engl. J. Med. 1983; 309: 331–336).

Thus, despite the major advances made over the past few years in the treatment of myocardial infarction, the prognosis remains fairly guarded in patients who show a major impairment of the ventricular function which is reflected by a marked decrease in the ejection fraction at this level.

Although this prognosis is more favorable in patients with an ejection function greater than 40%, it deteriorates gradually as this parameter tends towards the critical threshold of 40%. Death, which is often sudden in these patients, is very probably caused in most cases by a ventricular fibrillation degenerating into lethal ventricular tachycardia.

In these cases, it seems, consequently, logical to try to prevent these ventricular disorders by the administration of antiarrhythmic agents. Unfortunately, all attempts to reduce post-infarction mortality with class I antiarrhythmic agents (Vaughan-Williams classification) most widely used has failed especially in patients with arrhythmias or with reduced left ventricular fraction (The CAST Investigators— N. Engl. J. Med. 1989; 321: 406–412).

On the contrary, these antiarrhythmic agents should be contraindicated since instead of reducing the mortality following myocardial infarction, they in fact increase the number of sudden deaths, probably because of their arrhythmogenic effects.

Following these observations, the great majority of cardiologists have been skeptical and even opposed to the concept of prevention of sudden death following myocardial infarction by the administration of antiarrhythmic agents.

Amiodarone, a potent corrector of rhythm disorders widely used in this indication, is capable of substantially suppressing the complex premature ventricular contractions and the sustained ventricular tachycardia while only exhibiting a little marked negative inotropic effect and being considerably less arrhythmogenic than the class I antiarrhythmics.

However, amiodarone differs from other antiarrhythmic agents in a different mechanism of action: its ability to prolong the duration of the action potential and to extend the refractory period for the myocardial cell places it in the category of Vaughan-Williams class III antiarrhythmics.

While it is perfectly recognized that amiodarone is a beneficial agent in potentially fatal arrhythmias which are often refractory to the other antiarrhythmics, its efficacy has also been evaluated in the prevention of deaths occurring after myocardial infarction.

For example, L. Ceremuzinski et al. (J. Am. Coll. Cardiol. 1992; 20: 1056–1062) have recorded, after administration of amiodarone at the dose of 200 mg/day for one year, a significant reduction in the post-infarction mortality and ventricular arrhythmias in high-risk patients with a contraindication to the prescription of β-blockers whereas in the CAMIAT study (Circulation 1991; 84: 550–557), J. A. Cairns et al. observed, at the dose of 300 to 400 mg/day, a tendency of amiodarone to exhibit a beneficial effect towards especially the total mortality or the mortality of cardiac origin in patients having ventricular extrasystoles after myocardial infarction.

In the BASIS study (J. Am. Coll. Cardiol. 1990; 16: 1711–1718), F. Burkart et al., for their part, studied for one year the effects of amiodarone at the dose of 200 mg/day in myocardial infarction survivors having arrhythmias. However, the beneficial effects recorded must be weighed against a lack of efficacy observed in patients with reduced left ventricular function, that is to say with an ejection fraction of less than or equal to 40%.

The main benefit of this study lies, consequently, in the demonstration of an amiodarone effect on the survival of patients having asymptomatic complex ventricular arrhythmias with preserved left ventricular function (ejection fraction ≧40%).

Consequently, the left ventricle ejection fraction appears to be more involved in the prognosis of survival of the patient than the ventricular arrhythmias, in agreement with C. S. Chakko et al. (Am. Heart J. 1985; 109: 497–504).

Moreover, clinical trials carried out in patients who have not had myocardial infarction have sometimes highlighted different results.

For example, small preliminary studies undertaken with amiodarone in patients suffering from cardiomyopathies, ventricular arrhythmias or cardiac insufficiency have given contradictory results: Neri et al. (Am. Heart J. 1987; 113: 707–715) recorded an improved survival, Cleland et al. (Br. Heart J. 1987; 58: 572–582) reported a reduced incidence of sudden death whereas Nicklas et al. (Am. Heart J. 1991; 122: 1016–1021) as well as Stewart et al. (Brit. Heart J. 1989; 61: 459–460) observed no improvement.

Likewise, in another study carried out in patients suffering in this case from severe cardiac insufficiency, the GESICA study, H. C. Doval et al. (Lancet 1994; 344: 493–498) showed that amiodarone, at the dose of 300 mg/day, for 2 years, made it possible to obtain a significant reduction in mortality in the treated group compared with the control group whether for sudden death or for mortality due to progressive cardiac insufficiency.

Finally, S. N. Singh et al. have published in N. Engl. J. Med. 1995; 333: 77–82, the results of the CHF-STAT clinical study extending over 45 months with daily doses of 300 mg of amiodarone in patients having asymptomatic ventricular arrhythmias and suffering from moderate cardiac insufficiency of ischaemic or nonischaemic origin.

Although this compound proved effective for suppressing ventricular arrhythmias and improving ventricular function, this study showed, completely unexpectedly, that amiodarone has no effect, after 2 years, either on sudden death or on the prolonging of the survival of patients having a moderate cardiac insufficiency.

However, it has been possible to reveal a tendency to reduce the mortality in patients with nonischaemic cardiomyopathy (ejection fraction $\geq 40\%$).

Attempts to interpret the apparently contradictory results highlighted in these last two trials have been formulated by G. Breithardt (N. Engl. J. Med. 1995; 333: 121–122) and by S. C. Hammill et al. (Heart 1996; 75: 6–7).

These authors have pointed out that the most significant difference between the two studies lies in the actual nature of the underlying cardiac disease.

In fact, the great majority of patients in the CHF-STAT trial had an ischaemic cardiomyopathy whereas, on the contrary, a majority of patients in the GESICA study suffered from nonischaemic cardiomyopathy.

Consequently, and for this reason, the patients in the CHF-STAT study probably did not benefit from amiodarone. The tendency noted in the BASIS study mentioned above where a lack of efficacy of this compound had been observed in patients with ejection fraction <40% might therefore be confirmed by these trials.

It may therefore be concluded, following these clinical data, that the underlying cause of cardiac insufficiency may play a predominant role in the determination of a beneficial effect of amiodarone on the prophylaxis of the mortality.

Patent FR 2,626,176 can moreover be mentioned which relates to compositions intended for the treatment of coronary insufficiency by combination of amiodarone and at least one vasodilator and one β-blocker.

According to this patent, amiodarone and isosorbide dinitrate, taken separately, do not show, relative to a control group, a reduction in mortality either at 7 days or at 1 year, whereas the early administration, at the start of infarction, of the isosorbide dinitrate/amiodarone combination, followed by a prolonged administration of this same combination, is thought to reduce the mortality at 1 year in myocardial infarction.

Nevertheless, no comparative result is reported therein, which would make it possible to support this conclusion.

This assertion appears, consequently, purely speculative and all the more doubtful since it no longer appears in patent application WO 90/09176 by the same inventor who describes, subsequently, the same compositions intended for the treatment of coronary insufficiency.

Finally, there may be mentioned patent application WO 95/09625 which relates to the use of amiodarone for the treatment of patients suffering from cardiac insufficiency, whether they carry ventricular arrhythmias or otherwise. Amiodarone is possibly combined therein with other cardioactive agents.

However, no reference is made, in this patent application, to a left ventricular dysfunction as essential factor in the cause of mortality, such that it is totally impossible to deduce or even predict the behavior of amiodarone, combined or otherwise with other cardioactive agents, in the presence of this sole risk factor resulting from a lower left ventricular function.

From the results assembled above, it can be asserted that, to a certain extent, a benefit of amiodarone may be demonstrated on the prevention of mortality following myocardial infarction or otherwise and this, in patients having rhythm disorders and/or certain forms of cardiac insufficiency.

However, there has never been reported or even published up until now any advantage of amiodarone in the prevention of deaths by early administration of this agent after the acute phase of myocardial infarction, especially in the prevention of mortality of cardiac origin, in particular the cardiac mortality of arrhythmic origin, taking into account, as sole predominant and fatal risk factor, a left ventricular dysfunction which results from a low ejection fraction.

There may be mentioned, however, the publications by A. Munoz (Arch. Mal. Coeur 1991; 94 (II): 67–69) and by J. A. Camm et al. (Am. J. Cardiol. 1993; 72: 95F–98F) which describe a clinical study procedure involving the evaluation of amiodarone as agent for the prevention of mortality following myocardial infarction in patients not having arrhythmias during incorporation into the trial but an impaired left ventricular function.

The study in question requiring several years, no result whatsoever has yet been published which would make it possible to confirm or infirm the hypotheses which serve as basis thereto.

Accordingly, it can be concluded from all the studies reported above, that the behavior of amiodarone in relation to mortality in at-risk patients, whether they are in a post-infarction period or otherwise, is far from being elucidated all the more so since the sometimes surprising and divergent results have been recorded which allow the formulation of only simple suppositions on the still poorly known aspects of this antiarrhythmic.

However, it has now been found that amiodarone and its pharmaceutically acceptable salts are capable of preventing, significantly and with fewer arrhythmogenic effects than class I antiarrhythmics, certain types of mortality especially mortality of cardiac origin, in particular cardiac mortality of arrhythmic origin in patients having, following myocardial infarction, a reduced left ventricular function, that is to say patients with ischaemic cardiomyopathy, without symptomatic rhythm disorders.

Consequently, it can be confirmed that there has been demonstrated for the first time, within the framework of the present invention, the possibility of preventing cardiac mortality of arrhythmic origin, especially sudden death in the post-infarction period, by means of an antiarrhythmic agent, in this case amiodarone or its pharmaceutically acceptable salts, in patients with a major risk factor but without symptomatic arrhythmias.

The observed reduction in cardiac mortality of arrhythmic origin is visualized by a reduction in mortality of arrhythmic origin, especially a reduction in the number of sudden deaths.

Thus, the invention relates to a method for reducing mortality of cardiac origin in patients having a reduced left ventricular function after myocardial infarction, without rhythm disorders requiring an antiarrhythmic treatment, consisting in administering to said patients an effective amount of one or more active ingredients selected from benzofuran derivatives with antiarrhythmic activity and pharmaceutically acceptable salts thereof in combination with one or more pharmaceutically acceptable vehicles.

"Benzofuran derivative with antiarrhythmic activity" designates, within the framework of the present invention, a benzofuran compound selected from those described in patents U.S. Pat. No. 3,248,401, U.S. Pat. No. 5,223,510 and EP 338746 as well as in patent applications WO 88/07996, WO 89/02892, WO 90/02743 and WO 94/29289.

From all these compounds, there may be mentioned for example 2-n-butyl-3-[4-(3-di-n-butylaminopropoxy)

benzoyl]-5-methylsulphonamidobenzo-furan or dronedarone and its pharmaceutically acceptable salts which are described in U.S. Pat. No. 5,223,510.

However, amiodarone and its pharmaceutically acceptable salts which are described in U.S. Pat. No. 3,248,410 is generally preferred as benzofuran derivative with antiarrhythmic activity.

In fact "amiodarone" is understood to mean, in the context of the present invention, 2-n-butyl-3-(4-diethylaminoethoxybenzoyl)benzofuran in basic form or in the form of inclusion complexes in cyclodextrins, their ethers or their esters.

The use of the active metabolites of the benzofuran derivatives with antiarrhythmic activity referred to above, also forms part of the present invention. As an example of such metabolites, there may be mentioned 2-n-butyl-3-(4-ethylaminoethoxybenzoyl)-benzofuran or N-desethylamiodarone and its pharmaceutically acceptable salts as described in patent FR 2,550,091 and 2-n-butyl-3-[4-(3-n-butylamino-propoxy)benzoyl]-5-methylsulphonamidobenzofuran or N-desbutyldronedarone and its pharmaceutically acceptable salts described in U.S. Pat. No. 5,223,510.

Likewise, the term "mortality of cardiac origin" covers, within the framework of the invention, the mortality due to any cardiac causes (any deaths except those due to a noncardiac cause) in particular, and more particularly, cardiac mortality of arrhythmic origin.

"Cardiac mortality of arrhythmic origin" in fact designates mortality, sudden or otherwise, due to any arrhythmic cause, that is to say either death occurring within an hour or less than an hour following the appearance of new symptoms in the absence of worsened left ventricular insufficiency or of shock, or death, without a witness, of an apparently stable patient, or fatal ventricular fibrillation ("nonresuscitated").

The term "cardiac mortality of arrhythmic origin" also covers, within the framework of the invention, nonfatal cardiac arrests ("resuscitated" after defibrillation), that is to say the nonfatal arrhythmic events causing a cardiac arrest.

Furthermore, the expression "cardiac mortality of arrhythmic origin" also includes more specifically "sudden cardiac mortality of arrhythmic origin" or "sudden mortality of arrhythmic origin" or "sudden death", namely death occurring within an hour or less than an hour following the appearance of new symptoms in the absence of worsened left ventricular insufficiency or the fortuitous death of a patient without symptoms or with stable cardiovascular symptoms which occurred without a witness and within 24 hours of knowing of this event.

It may also be specified that the expression "patient having a reduced left ventricular function following myocardial infarction, without rhythm disorders requiring an antiarrhythmic treatment" means a patient who, with a reduced left ventricular function after myocardial infarction, may possibly have asymptomatic rhythm disorders, that is to say without pathological significance but no rhythm disorders requiring an antiarrhythmic treatment.

Finally, "reduced left ventricular function" is understood to mean essentially a deficient left ventricular function reflected by an ejection fraction $\leq 40\%$.

As will be described in greater detail later, it has been observed during a trial involving several hundreds of patients, that amiodarone, preferably in the form of its hydrochloride, administered daily after the acute phase of myocardial infarction, does not cause any detrimental effect over a period of 24 months.

In addition, it has been found that this antiarrhythmic agent tends to prevent mortality of cardiac origin in some specific cases, for example in patients with an ejection fraction greater than 30% and less than or equal to 40% in a first infarction period, that is to say patients who have not had one or more previous infarctions.

Likewise, it has been possible to demonstrate that amiodarone hydrochloride can significantly prevent over a period of at least 2 years, cardiac mortality of arrhythmic origin, sudden or otherwise, comprising or not comprising nonfatal cardiac arrests, since it has been possible to record a reduction of 28 to 30% in this type of mortality at 2 years.

Moreover, it has been found that amiodarone hydrochloride may also reduce, quite significantly, sudden mortality of arrhythmic origin or sudden death over a period of 24 months (37% reduction at 24 months).

This prophylactic effect, which has also been observed in patients with an ejection fraction greater than 30% and less than or equal to 40%, even proved more marked in patients with a considerably reduced left ventricular ejection fraction, that is to say <30%.

For their use in therapy, the benzofuran derivatives with antiarrhythmic activity according to the invention are generally introduced into pharmaceutical compositions.

These pharmaceutical compositions may be provided in any form appropriate for their administration in human therapy, especially for administration by the oral, sublingual, nasal, inhaled, parenteral, topical, transdermal or rectal route.

Generally, the oral or parenteral route, preferably the oral route, is used. As regards the administerable unit, it may take the form, for example, of a tablet, scored or otherwise, a sugar-coated tablet, a capsule, a gelatine capsule, a powder, a suspension or a syrup for oral administration, of a suppository for rectal administration, of a solution or suspension for parenteral administration or of a device commonly called "patch" for transdermal administration.

The pharmaceutical compositions according to the invention may advantageously comprise, per administerable unit, from 50 to 600 mg of active ingredient, especially from 150 to 250 mg for oral administration, from 10 to 250 mg of active ingredient for parenteral administration or from 50 to 200 mg of active ingredient for rectal administration.

Pharmaceutical compositions may especially be prepared containing amiodarone, dronedarone or one of their pharmaceutically acceptable salts in an amount of 50 to 500 mg for oral administration, more particularly oral compositions containing from 150 to 250 mg of amiodarone or one of its pharmaceutically acceptable salts or from 50 to 150 mg of dronedarone or one of its pharmaceutically acceptable salts.

According to the route of administration chosen, the pharmaceutical compositions in question will be conventionally prepared by combining the active ingredient, such as amiodarone or dronedarone or one of their pharmaceutically acceptable salts, with an appropriate pharmaceutical excipient or vehicle, it being possible for the latter to consist, for example, of at least one ingredient selected from the following substances:

lactose, starches, talc, magnesium stearate, polyvinylpyrrolidone, alginic acid, colloidal silica, polysorbate, mannitol, sodium dihydrogen phosphate, distilled water, benzyl alcohol or sweetening agents.

For the preparation of an oral pharmaceutical composition, the active ingredient may for example be mixed with the pharmaceutical excipients or vehicles selected and then subjected to a dry or wet granulation.

According to the nature of the excipient used, it is possible, if necessary, to obtain, simply by mixing, a powder capable of being directly converted to tablets. This powder or this granule may be introduced directly into capsules or gelatine capsules, or preferably they may be converted, by compression, into tablet cores.

By way of example, pharmaceutical compositions may be prepared containing doses of 200 mg of amiodarone hydrochloride for administration by the oral route, for example, in the form of tablets, scored or otherwise, by granulation and compression of the following ingredients:

Example 1

| | | |
|---|---|---|
| Amiodarone hydrochloride | 200 mg | |
| Lactose | 96 mg | |
| Maize starch | 60 mg | |
| Polyvinylpyrrolidone | 12 mg | |
| Anhydrous colloidal silica | 2.4 mg | |
| Magnesium stearate | 4.6 mg | |
| | 375 mg | |

Example 2

| | | |
|---|---|---|
| Amiodarone hydrochloride | 200 mg | |
| Lactose | 71 mg | |
| Maize starch | 66 mg | |
| Polyvinylpyrrolidone | 6 mg | |
| Anhydrous colloidal silica | 2.4 mg | |
| Magnesium stearate | 4.6 mg | |
| | 350 mg | |

Likewise, a pharmaceutical composition may be prepared containing 106 mg of dronedarone hydrochloride for oral administration especially in the form of a gelatine capsule:

Example 3

| | | |
|---|---|---|
| Dronedarone hydrochloride (that is to say 100 mg of dronedarone base) | 106 mg | |
| Maize starch | 138.5 mg | |
| Talc | 50 mg | |
| Anhydrous colloidal silica | 1.25 mg | |
| Magnesium stearate | 2.5 mg | |
| Lactose | 201.75 mg | |
| | 500 mg | |

For a parenteral administration, pharmaceutical compositions may also be prepared containing doses of 150 mg of amiodarone hydrochloride or 10.6 mg of dronedarone hydrochloride, for example in the form of an injectable solution of formulation:

Example 4

| | | |
|---|---|---|
| Amiodarone hydrochloride | 150 mg | |
| Polysorbate 80 | 300 mg | |
| Benzyl alcohol | 60 mg | |
| Water for injection sq* | 3 ml | |

Example 5

| | | |
|---|---|---|
| Dronedarone hydrochloride (that is to say 10 mg of dronedarone base) | 10.6 mg | |
| Mannitol | 200 mg | |
| Anhydrous sodium dihydrogen phosphate | 120 mg | |
| Water for injection sq* | | |

*sq: sufficient quantity for

During the search for a prophylactic effect on post-infarction mortality, in agreement with the invention, the active ingredient, more specifically amiodarone or its pharmaceutically acceptable salts, may be administered at daily doses ranging from 100 to 800 mg by the oral route, preferably from 200 to 400 mg.

In the specific case of administration of amiodarone, or its pharmaceutically acceptable salts, by the oral route, daily doses greater than 400 mg, for example doses of 400 to 800 mg, especially doses of 600 to 800 mg, are reserved for treatment of short duration, for example by priming treatments requiring a large loading dose of active ingredient, whereas daily doses of less than or equal to 400 mg, for example doses of 200 to 300 mg, preferably doses of 200 mg are more representative of maintenance doses.

In particular, it is possible to use the following therapeutic scheme which comprises the administration of amiodarone hydrochloride as active ingredient first as a loading dose and then as a maintenance dose, namely:

Priming treatment: 800 mg/day or 4 tablets each containing 200 mg doses of amiodarone hydrochloride for 2 weeks, the treatment starting early after the acute phase of myocardial infarction, for example as early as the 5th day.

Maintenance treatment: 400 mg/day or 2 tablets each containing 200 mg doses of amiodarone hydrochloride for 3 to 4 months and then 200 mg of amiodarone hydrochloride for at least 12 months.

According to another aspect of the invention, the administration of the benzofuran derivative with antiarrhythmic activity or of one of its pharmaceutically acceptable salts may be performed in close, that is to say simultaneous or sequential, association with the administration of at least one additional cardioactive agent so as to reinforce the desired prophylactic effect and/or to treat the underlying cardiac disease.

Consequently, another subject of the invention relates to the use of a benzofuran derivative with antiarrhythmic activity, preferably amiodarone or dronedarone, or of a pharmaceutically acceptable salt of this derivative, for the preparation of pharmaceutical compositions to be administered in simultaneous or sequential association with at least one additional cardioactive agent, for the reduction of mortality of cardiac origin in patients having a reduced left ventricular function following myocardial infarction, without rhythm disorders requiring an antiarrhythmic treatment.

According to this variant, the active ingredient, for example amiodarone, dronedarone or one of their pharmaceutically acceptable salts, may be associated with at least one additional cardioactive agent selected from a diuretic, an angiotensin converting enzyme inhibitor, an angiotensin II inhibitor, a calcium inhibitor, a cardiotonic agent, a β-blocking agent, a nitro derivative and a vitamin K inhibitor.

By way of nonlimiting examples, there will be mentioned hereinafter cardioactive agents which may be associated with the active ingredient in question, these agents being called by their International Nonproprietary Name (INN).

Thus, there may be selected:

the diuretic from furosemide, hydrochlorothiazide, metolazone, amiloride and spironolactone, these compounds being administered at therapeutically active doses chosen between 1 and 200 mg/day, the angiotensin converting enzyme inhibitor from captopril, enalapril, fosinopril, quinapril, ramipril, lisinopril, cilazapril and perindopril, these compounds being administered at therapeutically active doses chosen between 2 and 150 mg/day, the angiotensin II inhibitor from irbesartan, losartan, candesartan, valsartan, zolasartan, telminsartan, eprosartan, these compounds being administered at therapeutically active doses chosen between 1 and 200 mg/day. However, irbesartan represents a preferred angiotensin II inhibitor, the calcium inhibitor from nifedipine, nicardipine, lacidipine, felodipine, amlodipine, diltiazem and verapamil, these compounds being administered at therapeutically active doses chosen between 1 and 500 mg/day, the cardiotonic agent from acetyldigitoxin, digitoxin and digoxin, these compounds being administered at therapeutically active doses chosen between 0.1 and 2 mg/day, the β-blocking agent from timolol, atenolol, pindolol, bisoprolol, acebutolol, propranolol, metoprolol, nadolol, tertatolol, alprenolol, betaxolol, celiprolol and oxprenolol, these compounds being administered at therapeutically active doses chosen between 10 and 500 mg/day, the nitro derivative from nicorandil, isosorbide mononitrate, isosorbide dinitrate and trinitrin, these compounds being administered at therapeutically active doses chosen between 2 and 200 mg/day, the vitamin K antagonist from warfarin, acenocoumarole and phenprocoumone, these compounds being administered at therapeutically active doses chosen between 1 and 50 mg/day.

The associations with an angiotensin converting enzyme inhibitor or with an angiotensin II inhibitor represent, however, preferred associations.

However, amiodarone or its pharmaceutically acceptable salts, do not represent the preferred benzofuran derivative with antiarrhythmic activity for the preparation, for example, of a simultaneous association represented by a single administerable unit given its particularly prolonged lifetime compared with the other cardioactive agents which would be associated with it.

The prophylactic efficacy of the benzofuran derivatives with antiarrhythmic activity and their pharmaceutically acceptable salts in relation to post-infarction mortality has been demonstrated using amiodarone hydrochloride, during a double blind (with a triple blind approach) multicentre prospective clinical study with randomization of the patients into 2 defined groups using the left ventricular ejection fraction.

This study, which was spread over a period of several years, was performed on high-risk patients with a deficient left ventricular function after a recent myocardial infarction. It consisted in demonstrating, over a period of 2 years, a reduction in cardiac mortality, cardiac mortality of arrhythmic origin concurrent or otherwise with nonfatal arrhythmic events causing a cardiac arrest and finally a reduction in sudden mortality of arrhythmic origin (sudden death).

CLINICAL STUDY

I. Selection of the patients

The randomization of the patients was performed between the 5th and 21st days following the myocardial infarction. During this period, the following inclusion and exclusion criteria were checked for each patient of both sexes capable of being enrolled in the trial, namely:

Inclusion criteria 1) presence of a myocardial infarction
2) ejection fraction less than or equal to 40% by standardized radionuclide ventriculography
3) age more than 18 years and less than 75 years A Holter recording was also performed for 24 hours but the results were not retained for inclusion.

Exclusion criteria 1) contraindications for amiodarone
2) specific status of the patient, especially women of reproductive age, noncardiac or pre-existing disease capable of significantly shortening a survival for 2 years or any condition requiring a treatment with tricyclic antidepressants, phenytoin, lidoflazine, prenylamine or vincamine
3) need for an antiarrhythmic therapy other than β-blockers or digitalis at the time of inclusion in the trial
4) severe angina not responding to a conventional treatment
5) serious cardiac insufficiency not responding to a conventional treatment
6) need for a cardiac surgery Each of the 1486 patients selected according to these criteria were included in the study and randomized into two groups between 5 and 21 days following the myocardial infarction so as to receive either amiodarone hydrochloride or the placebo. These groups were formed on the basis of the ejection fraction, that is to say:

a group of 797 patients having an ejection fraction greater than 30% and equal to or less than 40%, hereinafter "Group I"

a group of 689 patients having an ejection fraction of less than 30%, hereinafter "Group II".

II. Duration and treatment

The trial lasted for 4 years, the period of recruitment being spread over 3 years so that the patients recruited during the first 2 years were treated for 2 years and those recruited during the last year were treated up to the end of the trial. The minimum treatment was, consequently, 1 year. This treatment was introduced according to a double blind design using tablets containing either the placebo or 200 mg of amiodarone hydrochloride, according to the following therapeutic scheme:

a) Loading dose:

800 mg, that is to say 4 tablets/day in two doses for 2 weeks.

b) Maintenance dose:

400 mg, that is to say 2 tablets/day in two doses from the 3rd week for 3 months and 2 weeks.

200 mg, that is to say 1 tablet/day for 20 months.

A co-medication was also introduced, namely: angiotensin converting enzyme inhibitors in 77% of the patients, β-blockers in 44%, vitamin K antagonists in 29%, digoxin in 23%, calcium antagonists in 14%.

Holter recordings performed during the trial, showed that about 40% of the patients had more than 10 ventricular premature beats per hour or 3 consecutive premature beats.

III. Results

The differences in survival recorded were analyzed by the Kaplan-Meyer method (p significant if $\leq 0.05$).

By taking into account:

the total mortality in the trial, that is to say the mortality due to any cause whether cardiac, noncardiac or unknown or the total cardiac mortality, that is to say the mortality due to cardiac causes, no significant difference was recorded, over a period of 24 months, between the rate of survival in the treated group and the rate of survival in the placebo group. However, no detrimental effect caused by amiodarone hydrochloride was observed over the period considered. In addition, no significant reduction in total mortality was observed in Groups I and II over the same 24-month period. However, it was possible to demonstrate an early preventive effect of the total mortality in Group I over the period of the first 6 months (p=0.06) and especially over the period of the first 3 months (p<0.05).

Moreover, no significant effect of reduction in total mortality was observed, compared with the placebo group, over a period of 24 months in patients with one or more previous infarctions.

However, a tendency to prevent total mortality in patients with a first infarction was able to be noted over the same 24-month period (p<0.05 over 3 months, p=0.06 over 6 months and p=0.07 over 12 months).

Other results obtained during this randomized trial are presented below with reference to the accompanying drawings in which.

a) the abbreviations used have the following meanings:
"PL" means "placebo"
"Am" and "amiodarone" mean "amiodarone hydrochloride"
"St. 1" means "Group I"
"St. 2" means "Group II"
"MI" means "one or more previous myocardial infarctions"
"noMi" means "first myocardial infarction"
"*" means p<0.05
"**" means p<0.01.

BRIEF DESCRIPTION OF THE DRAWINGS b)

Figure 1:
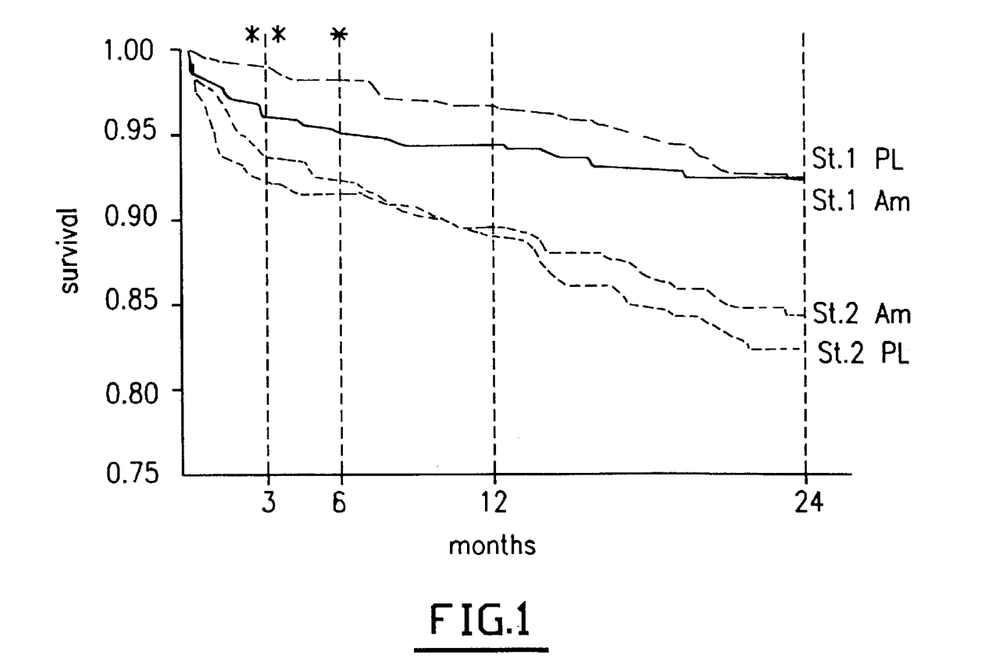
FIG. 1 represents the number of patients in Groups I and II surviving, for 24 months, death of cardiac origin.

These results show that amiodarone hydrochloride does not significantly reduce, compared with the placebo group, the rate of mortality of cardiac origin over a period of 24 months in the 2 groups in question. However, an early prophylactic effect was able to be demonstrated during the first 6 months in Group I (p<0.05 over 6 months) and more particularly in the first 3 months (p<0.01 over 3 months).

Figure 2:
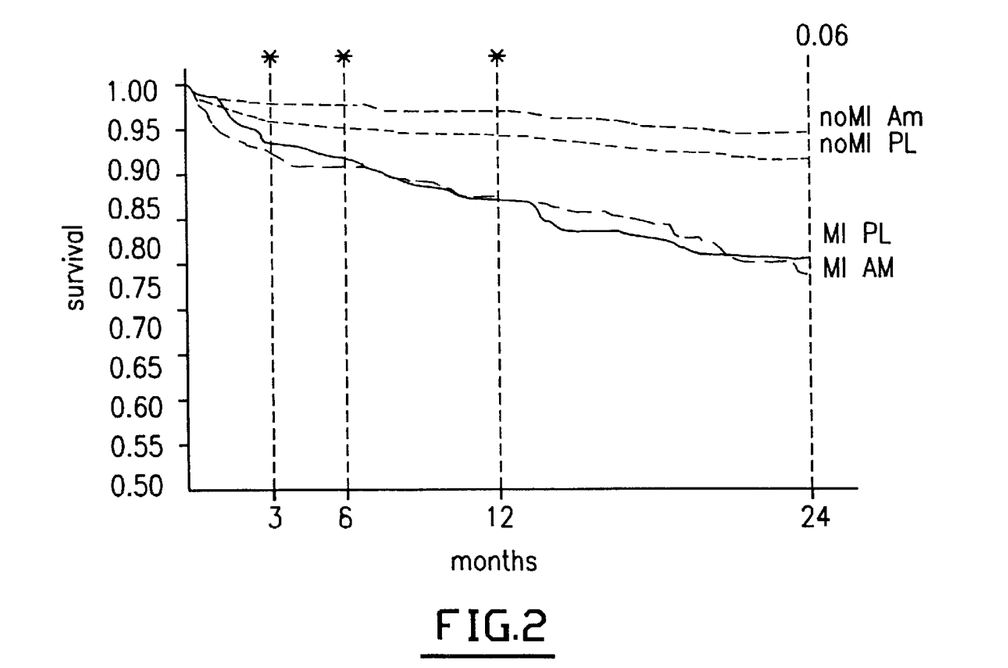
FIG. 2 represents the number of patients surviving, for 24 months, cardiac death following inaugural infarction.

No significant effect of reduction in mortality of cardiac origin over a period of 24 months in patients with a history of infarction, is observed following this trial and compared with the placebo group. On the other hand, a tendency to prevent mortality of cardiac origin in patients without a history of infarction was able to be detected over the same period of 24 months (p=0.06 over 24 months) whereas a significant reduction in this type of mortality was noted over a period of 3 months, 6 months and 12 months (p<0.05 over 3, 6 and 12 months).

Figure 3:
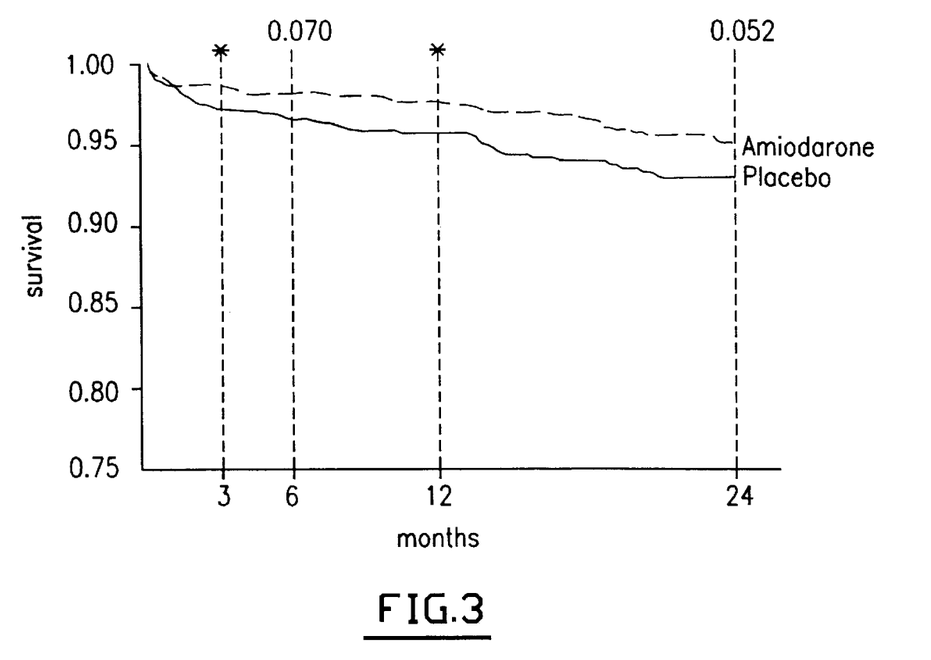
FIG. 3 represents the number of patients surviving cardiac death of arrhythmic origin over a period of 24 months.

The results obtained show a significant reduction in this type of mortality, compared with the placebo group, over a period of 3 months (p<0.05), 6 months (p<0.05) and 24 months (p=0.052).

For example, a 44% reduction in cardiac mortality of arrhythmic origin was obtained at 6 months and 30% at 24 months.

Figure 4:
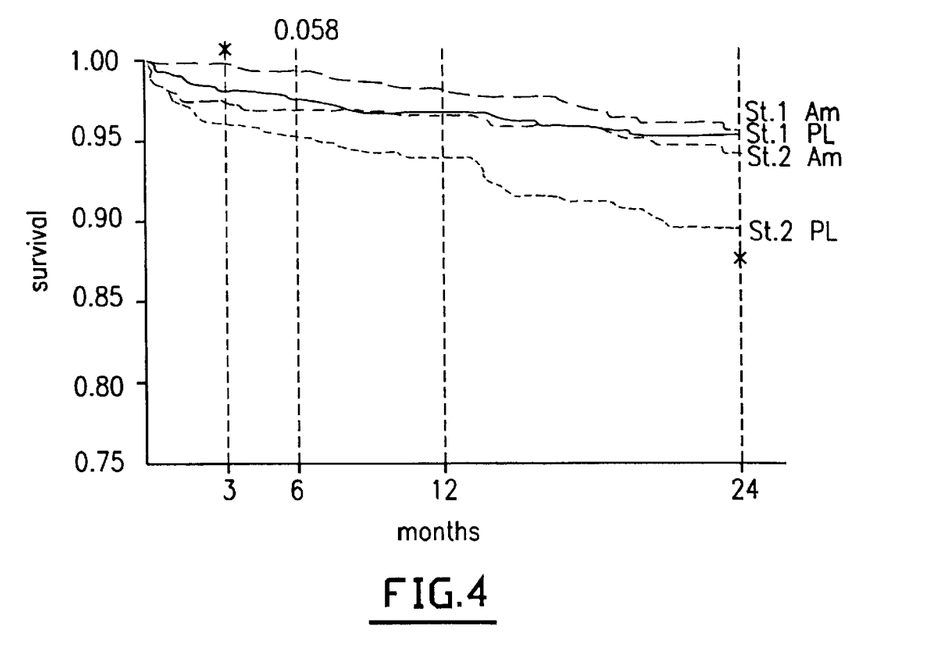
FIG. 4 represents the number of patients in Groups I and II surviving, over a period of 24 months, cardiac death of arrhythmic origin. A significant reduction in this type of mortality, compared with the placebo group over a period of 3 months (p<0.05) and 6 months (p=0.058) in Group I and over a period of 24 months (p<0.05) in Group II, can be deduced from these results.

Thus, a significant prophylactic effect was observed which was even more marked in Group II than in Group I, that is to say in patients with a particularly reduced left ventricular ejection fraction (<30%).

Figure 5:
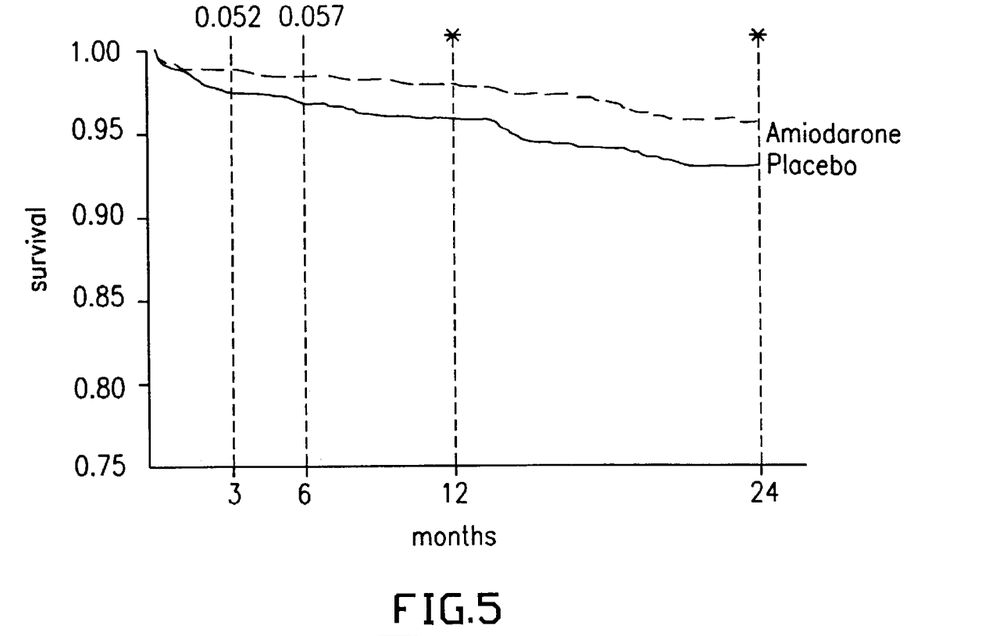
FIG. 5 represents the number of patients surviving sudden death of arrhythmic origin over a period of 24 months.

The results obtained highlight a significant reduction in this type of mortality compared with the placebo group (p=0.052 over 3 months, 0.057 over 6 months, <0.05 over 12 months and <0.05 over 24 months).

In addition, the following % reduction in this type of mortality was recorded:
53% reduction at 3 months
48% reduction at 6 months
48% reduction at 12 months
37% reduction at 24 months g)

Figure 6:
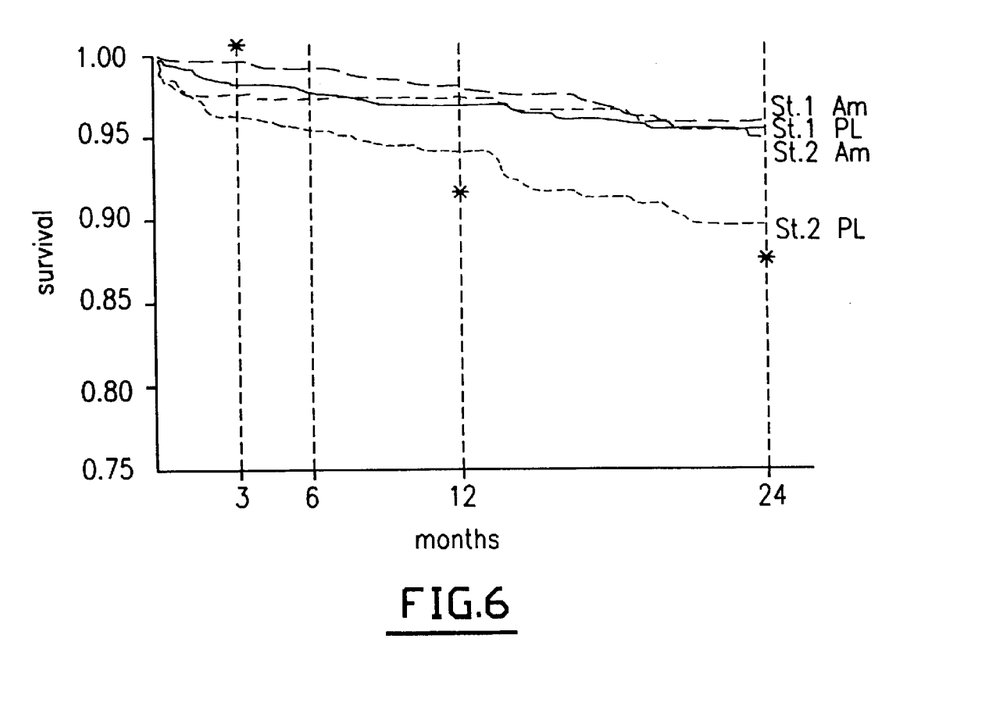
FIG. 6 represents the number of patients in Groups I and II surviving, over a period of 24 months, sudden death of arrhythmic origin.
Figure 7:
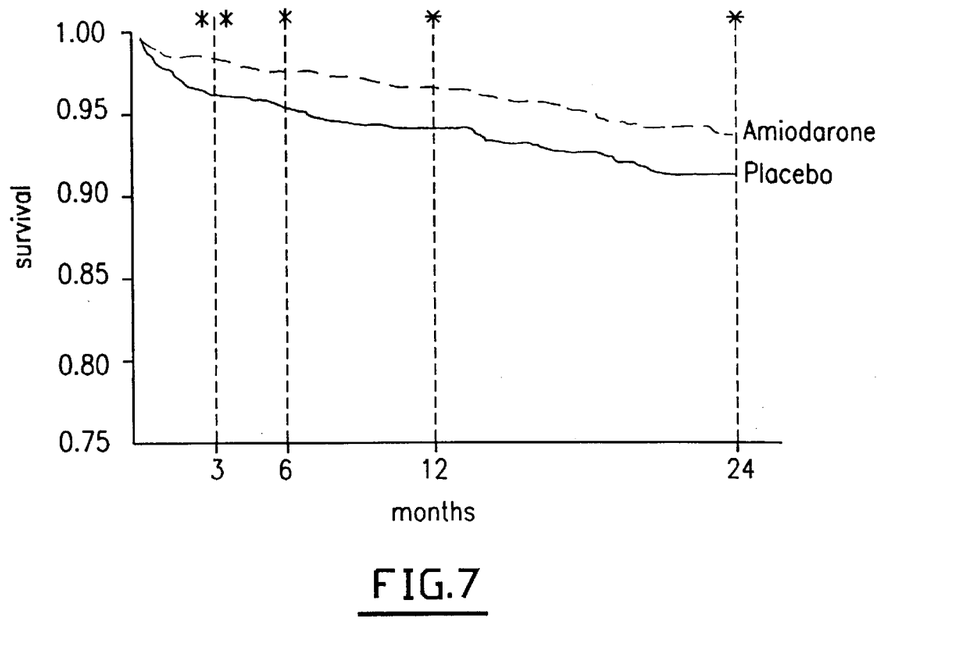
FIG. 7 represents the cumulative number of patients surviving over a period of 24 months, either cardiac death of arrhythmic origin or nonfatal cardiac arrests.

Compared with the placebo, a significant reduction in this type of mortality was recorded, over the period considered, in the two groups having received amiodarone hydrochloride. However, an even more marked reducing effect was noted in Group II (p<0.05 over 12 months and over 24 months), that is to say in the group of patients having a highly reduced ejection fraction (<30%).

These results demonstrate a significant reduction over a period of 24 months, in this type of event compared with the placebo group (p<0.01 over 3 months and p<0.05 over 6 months, 12 months and 24 months). In addition, the following % reduction was recorded:
59% reduction at 3 months
45% reduction at 6 months
41% reduction at 12 months
28% reduction at 24 months 1)

Figure 8:
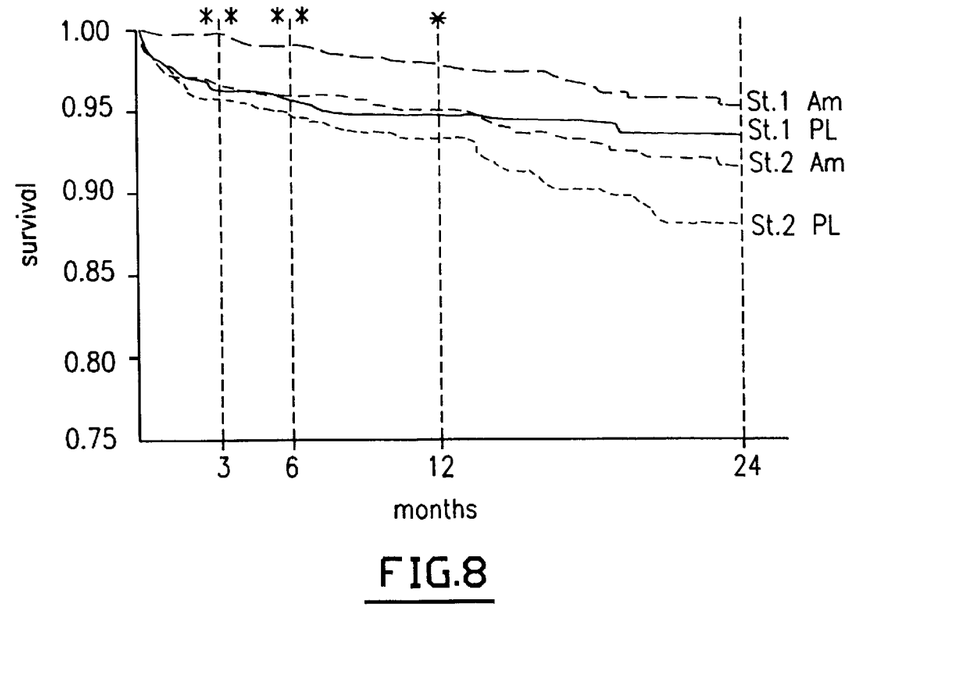
FIG. 8 represents the cumulative number of patients in Groups I and II surviving, over a period of 24 months, either cardiac death of arrhythmic origin or non-fatal cardiac arrests.

In Group II, a tendency to prevent this type of event was noted over a period of 24 months whereas in Group I, a significant reduction in this type of event was obtained with amiodarone hydrochloride compared with the placebo group over a period of at least 12 months (p<0.01 over 3 and 6 months and p<0.05 over 12 months).

We claim:

1. Method for reducing mortality of cardiac origin, or nonfatal cardiac arrests effected by an arrhythmic event, in a patient having reduced left ventricular function after myocardial infarction, without rhythm disorders requiring antiarrhythmic treatment, comprising administering to said patient an effective amount of one or more active ingredients selected from the group consisting of benzofuran derivatives with antiarrhythmic activity and pharmaceutically acceptable salts, thereof, in combination with one or more pharmaceutically acceptable vehicles.

2. Method according to claim 1, wherein the active ingredient is amiodarone or one of its pharmaceutically acceptable salts.

3. Method according to claim 1, wherein the active ingredient is dronedarone or one of its pharmaceutically acceptable salts.

4. Method according to claim 1, wherein the active ingredient is desethylamiodarone or one of its pharmaceutically acceptable salts.

5. Method according to claim 1, wherein the active ingredient is N-desbutyldronedarone.

6. Method according to claim 1, wherein the active ingredient is in the form of its hydrochloride salt.

7. Method according to claim 1, wherein the active ingredient is amiodarone hydrochloride.

8. Method according to claim 1 for reducing mortality of cardiac origin, wherein said mortality is cardiac mortality of arrhythmic origin.

9. Method according to claim 1 for reducing non-fatal cardiac arrest effected by an arrhythmic event.

10. Method according to claim 8, wherein the cardiac mortality of arrhythmic origin is sudden mortality of arrhythmic origin.

11. Method according to claim 1 in patients having a reduced left ventricular function reflected by an ejection fraction $\leq 40\%$.

12. Method according to claim 11, wherein the ejection fraction is greater than 30% and equal to or less than 40%.

13. Method according to claim 11, wherein the ejection fraction is less than 30%.

14. Method according to claim 1, wherein the active ingredient is administered by the oral, sublingual, nasal, inhaled, parenteral, topical, transdermal, or rectal route.

15. Method according to claim 14, wherein the active ingredient is administered by the oral route.

16. Method according to claim 14, wherein the active ingredient is administered by the parenteral route.

17. Method according to claim 15, wherein from 50 to 600 mg of active ingredient are administered.

18. Method according to claim 16, wherein from 10 to 250 mg of active ingredient are administered.

19. Method according to claim 15, wherein daily doses of 100 to 800 mg of amiodarone or one of its pharmaceutically acceptable salts are administered.

20. Method according to claim 19, wherein daily loading doses of 400 to 800 mg of amiodarone or of one of its pharmaceutically acceptable salts are administered.

21. Method according to claim 19, wherein daily maintenance doses of 200 to 300 mg of amiodarone or one of its pharmaceutically acceptable salts are administered.

22. Method according to claim 21, wherein the daily maintenance dose is 200 mg.

23. Method according to claim 1 further comprising the simultaneous or sequential administration of one additional cardioactive agent.

24. Method according to claim 23, wherein the additional cardioactive agent is selected from the group consisting of a diuretic, an angiotensin-converting-enzyme inhibitor, an angiotensin II inhibitor, a calcium inhibitor, a cardiotonic agent, a β-blocking agent, a nitro derivative, and a vitamin K inhibitor.

25. Method according to claim 24, wherein:
the diuretic is selected from the group consisting of furosemide, hydrochlorothiazide, metolazone, amiloride, and spironolactone;
the angiotensin converting enzyme inhibitor is selected from the group consisting of captopril, enalapril, fosinopril, quinapril, ramipril, lisinopril, cilazapril, and perindopril;
the angiotensin II inhibitor is selected from the group consisting of irbesartan, losartan, candesartan, valsartan, zolasartan, telminsartan, and eprosarton;
the calcium inhibitor is selected from the group consisting of nifedipine, nicardipine, lacidipine, felodipine, amlodipine, diltiazem, and verapamil;
the cardiotonic agent is selected from the group consisting of acetyldigitoxin, digitoxin, and digoxin;
β-blocking agent is selected from the group consisting of timolol, atenolol, pindolol, bisoprolol, acebutolol, propranolol, metoprolol, nadolol, tertatolol, alprenolol, betaxolol, celiprolol, and oxprenolol;
the nitro derivative is selected from the group consisting of nicorandil, isosorbide mononitrate, isosorbide dinitrate, and trinitrin;
the vitamin K antagonist is selected from the group consisting of warfarin, acenocoumarole, and phenprocoumone.

26. Method according to claim 24, wherein the additional cardioactive agent is selected from the group consisting of an angiotensin-converting-enzyme inhibitor and an angiotensin II inhibitor.

27. Method according to claim 26, wherein the angiotensin II inhibitor is irbesartan.

28. Method according to claim 23, wherein the active ingredient is amiodarone or one of its pharmaceutically acceptable salts.

29. Method according to claim 23, wherein the active ingredient is dronedarone or one of its pharmaceutically acceptable salts.

30. Method according to claim 23, wherein the active ingredient is in the form of its hydrochloride salt.

* * * * *